United States Patent
Weinstein et al.

(10) Patent No.: US 6,238,353 B1
(45) Date of Patent: May 29, 2001

(54) INCENTIVE SPIROMETER

(75) Inventors: Lawrence A. Weinstein, Oneida; Frederick M. Richards, Clinton, both of NY (US); James C. Wickstead, Mendham, NJ (US); Brian Forbes, Lincoln Park, NJ (US); Michael J. Keating, Blairstown, NJ (US)

(73) Assignee: DHD Healthcare Corporation, NY (US)

(*) Notice: Subject to any disclaimer, the term of this patent is extended or adjusted under 35 U.S.C. 154(b) by 0 days.

(21) Appl. No.: 09/382,608

(22) Filed: Aug. 25, 1999

(51) Int. Cl.$^7$ .................................................. A61B 5/08
(52) U.S. Cl. ............................... 600/540; 600/538
(58) Field of Search .......................... 600/540, 541, 600/538, 542, 543, 529, 533

(56) References Cited

U.S. PATENT DOCUMENTS

| | | |
|---|---|---|
| 436,665 | 9/1890 | Krell . |
| 3,063,183 | 11/1962 | Long . |
| 3,518,783 | 7/1970 | Foley . |
| 3,555,712 | 1/1971 | Yargeau . |
| 3,925,901 | 12/1975 | McCormick . |
| 4,086,918 * | 5/1978 | Russo ................................... 600/538 |
| 4,096,855 * | 6/1978 | Fleury, Jr. ............................. 600/540 |
| 4,114,608 * | 9/1978 | Russo ................................... 600/538 |
| 4,171,804 * | 10/1979 | Thead, Jr. ............................. 600/540 |
| 4,182,347 * | 1/1980 | Russo ................................... 600/538 |
| 4,232,683 * | 11/1980 | Bartholomew et al. ............. 600/538 |
| 4,284,083 * | 8/1981 | Lester ................................... 600/540 |
| 4,301,608 | 11/1981 | Taylor, Jr. . |
| 4,350,167 * | 9/1982 | Heimlich .............................. 600/540 |
| 4,391,283 * | 7/1983 | Sharpless et al. .................... 600/540 |
| 4,425,923 * | 1/1984 | Gordon et al. ....................... 600/540 |
| 4,499,905 * | 2/1985 | Greenberg et al. .................. 600/540 |
| 4,693,256 * | 9/1987 | Talonn ................................. 600/540 |
| 4,897,945 | 2/1990 | Webb . |
| 4,932,521 | 6/1990 | Au . |
| 5,022,170 | 6/1991 | House . |
| 5,113,612 | 5/1992 | Machen . |
| 5,276,986 | 1/1994 | Thomas . |
| 5,431,154 * | 7/1995 | Seigel et al. ......................... 600/540 |
| 5,984,873 * | 11/1999 | Crumb et al. ........................ 600/538 |

* cited by examiner

Primary Examiner—John P. Lacyk
Assistant Examiner—Navin Natnithithadha
(74) Attorney, Agent, or Firm—August E. Roehrig, Jr.; Hancock & Estabrook, LLP

(57) ABSTRACT

An improved incentive spirometer having a modular goal recording counter (GRC) releasably attached thereto for enabling a patient to view the number of times a predetermined respiratory therapy inhalation exercise has been properly performed. The GRC also includes a coaching lamp to facilitate the patient's maintaining the desired flow rate of inspiratory air for a predetermined time period. The GRC is operational in one mode to initiate a count of the number of successful exercise completions beginning with "0", and in another operational mode to retain and recall the count of the number of successful exercises previously completed. The operation of the GRC is controlled by a microcontroller which controls the operation of the GRC and the electrical circuit connected thereto is designed to minimize the power requirements of the components when the GRC is placed in the retain and recall mode of operation.

25 Claims, 7 Drawing Sheets

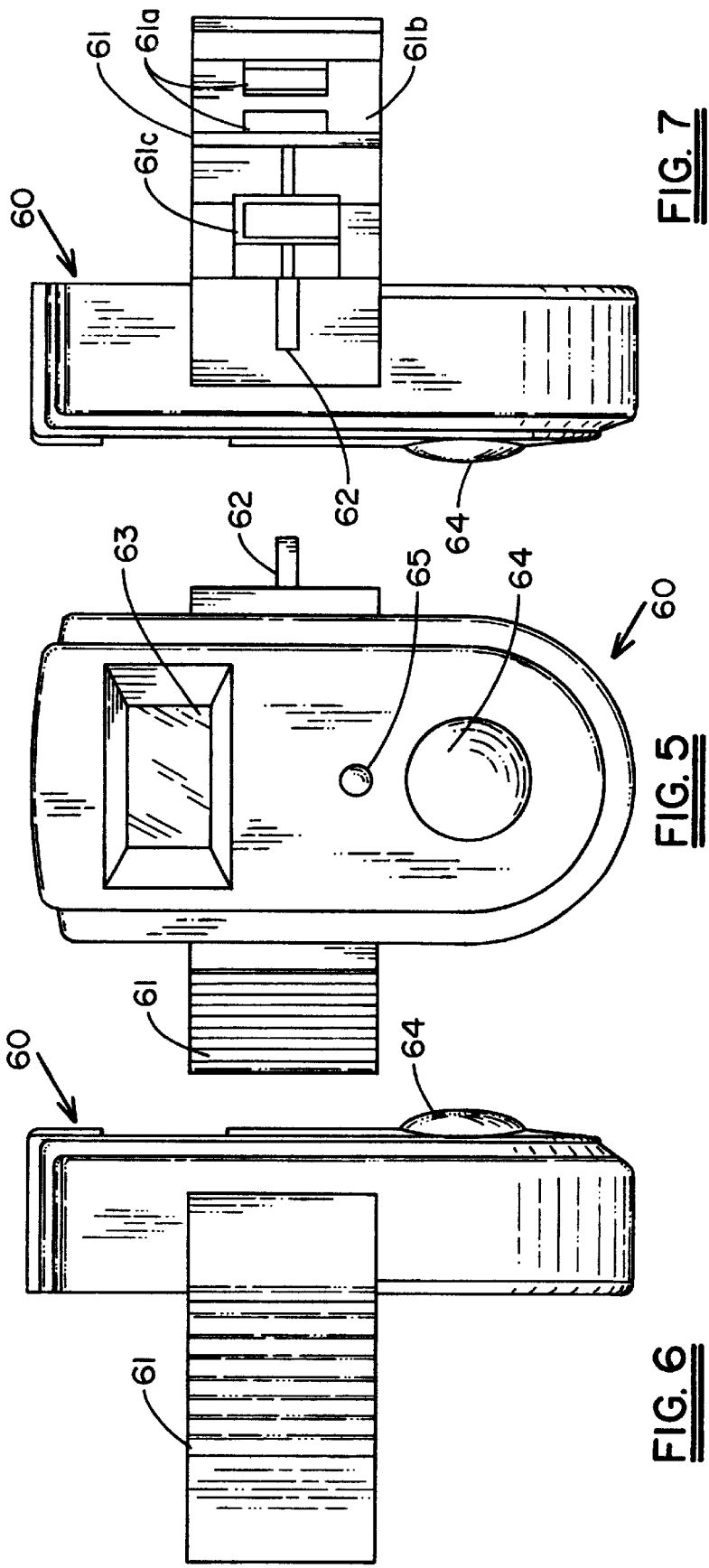

INCENTIVE SPIROMETER

BACKGROUND OF THE INVENTION

1. Field of the Invention

This invention relates in general to respiratory therapy devices and, in particular, to an improved incentive spirometer including a goal recording counter (GRC) which monitors the number of times a patient has completed a particular usage of the spirometer.

More specifically, but without restriction to the particular embodiment and/or use which is shown and described herein for purposes of illustration, this invention relates to an incentive spirometer having a detachable GRC which when applied to the spirometer records the number of times a user has successfully completed a particular breathing exercise. The spirometer also includes an oxygen inlet to facilitate the introduction of oxygen into the device without the oxygen effecting the monitoring of a patient's use of the device, and an integral information display receptacle to enable written information to be displayed while the spirometer is in use.

2. Description of Related Art

The use of incentive spirometers for respiratory care and treatment is well known. However, one of the desirable features for inclusion with such spirometers would be the incorporation of a counter to monitor the number of times that a user or patient has successfully completed a particular breathing exercise that has been prescribed for the patient's therapy or treatment. While certain spirometers have been designed to monitor functional operations, such equipment incorporates the monitoring function as an integral component of the spirometer or device with which the counter is used, or are actuable by the action of the user or patient when using the spirometer, thereby effecting the accuracy of the manner in which a patient is using the device. Accordingly, it would be desirable that such a monitor or counter be capable of accurately recording the number of times a patient or user has completed a particular exercise, but not interfere with or utilize the air stream between the patient and the breathing device. Incentive spirometers are utilized to monitor a patient's breathing, and to provide a controlled exercise for a patient's lungs and associated breathing apparatus. While the use of a counting device to record the number of times a patient has successfully completed a prescribed exercise is very advantageous when using an incentive spirometers, the interference with the air stream between the patient and the device can effect the calibration of the incentive spirometer, and gives the patient false feedback readings by which a patient monitors their proper use of the device. The present invention includes a removable Goal Recording Counter which is not an integral part of the spirometer and does not interfere with the calibration of the device or the patient's use of the spirometer.

SUMMARY OF THE INVENTION

It is an object of this invention to improve incentive spirometers.

Another object of this invention is to provide a spirometer which includes a GRC for monitoring or recording the number of times a patient has successfully completed a prescribed breathing exercise without interfering with the normal operation of the spirometer.

A further object of this invention is to provide a spirometer which includes a GRC for monitoring or recording the number of times a patient has successfully completed a prescribed breathing exercise without interfering with the calibration of the spirometer.

Still another object of this invention is to provide a spirometer which includes a GRC for monitoring or recording the number of times a patient has successfully completed a prescribed breathing exercise which is not an integral component of the spirometer, but can be removed therefrom for use with a separate device.

Yet another object of this invention is to provide a spirometer which includes a GRC for monitoring or recording the number of times a patient has successfully completed a prescribed breathing exercise and informing a patient that the exercise has been properly performed.

These and other objects are attained in accordance with the present invention wherein there is provided an improved incentive spirometer including a selectively removable Goal Recording Counter adapted to be positioned on the spirometer without interfering with the fluid communication between a patient and the spirometer to record the number of occurrences of a proper breathing exercise performed by a patient and to inform the patient when a predetermined exercise has been properly performed.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein:

FIG. 5 is a front elevational view of the Goal Recording Counter illustrated in FIG. 1 to better illustrate the features thereof;

FIG. 6 is a left side elevational view of the Goal Recording Counter illustrated in FIG. 5 to better illustrate the mechanism for connection to the spirometer body;

FIG. 7 is a right side elevational view of the Goal Recording Counter illustrated in FIG. 5 to better illustrate the mechanism for connection to the spirometer body;

Figure 1:
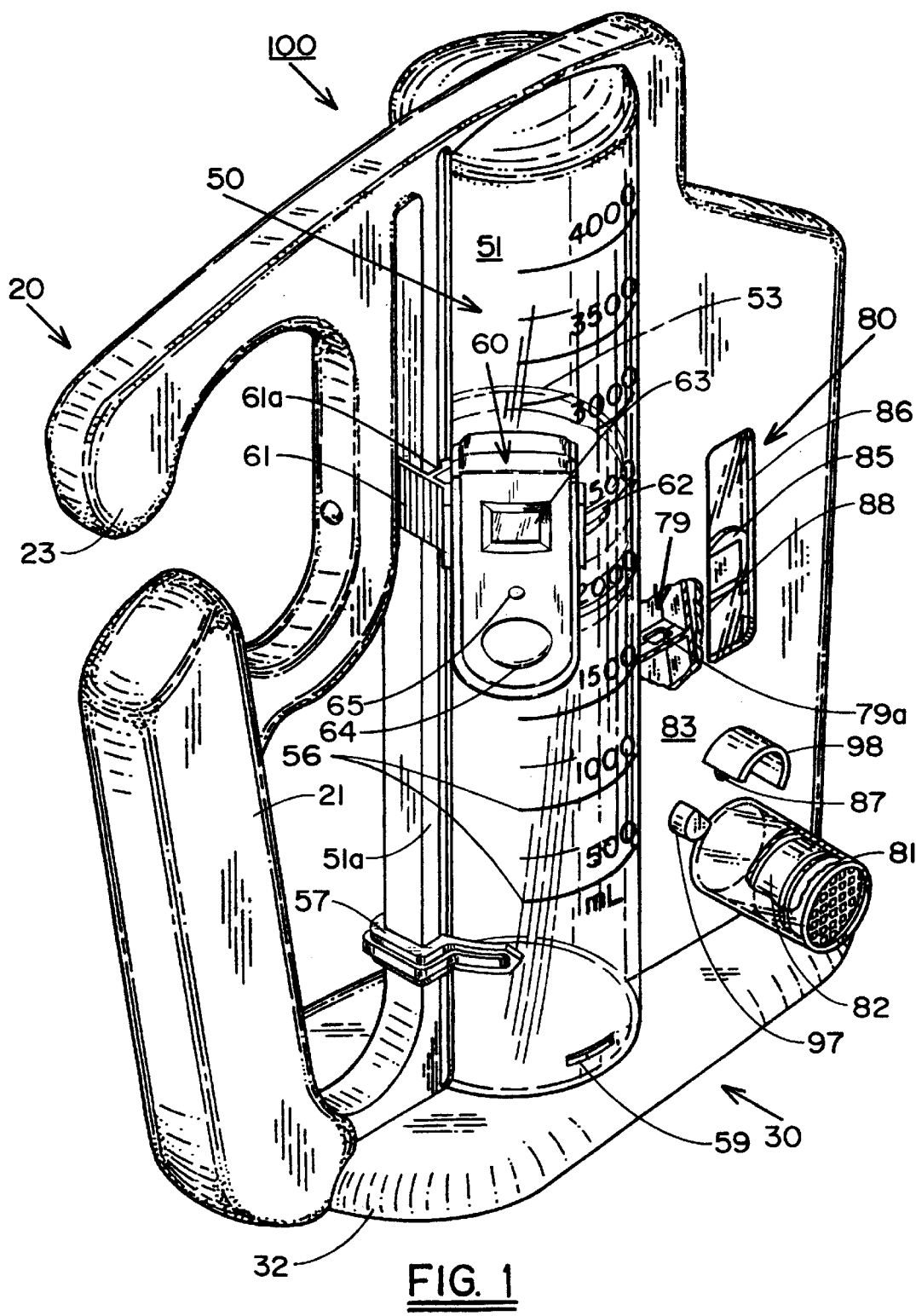
FIG. 1 is a frontal perspective view of the improved incentive spirometer with a GRC supported thereon in a position to record the occurrence of a properly performed exercise and to inform the patient when the exercise has been properly performed.
Figure 2:
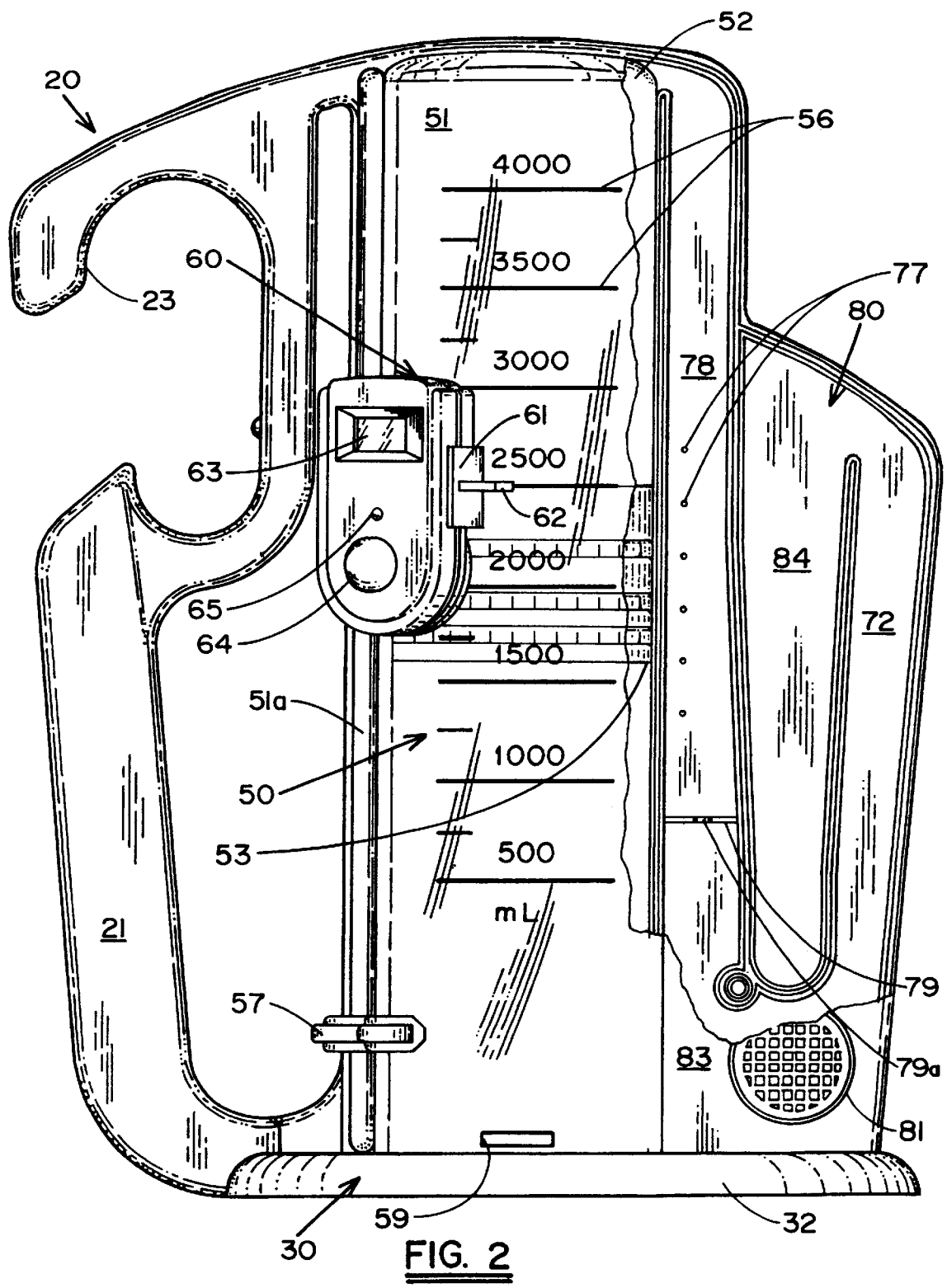
FIG. 2 is a frontal elevational view of the improved incentive spirometer illustrated in FIG. 1 with portions broken away to better illustrate the internal construction thereof.

These and additional embodiments of the invention may now be better understood by referring to the following detailed description of the invention wherein the illustrated embodiments are described.

DETAILED DESCRIPTION OF THE INVENTION

Throughout this description, the preferred embodiment and examples shown should be considered as exemplars, rather than limitations on the apparatus and methods of the present invention.

Referring now to the drawings, there is shown an incentive spirometer 100, having a handle portion 20, a base portion 30, a volume chamber portion 50, a goal recording counter (GRC) 60 and a monitoring portion 80. The handle portion 20 provides a convenient manner for holding and carrying the device, and for attaching the device to a bed, for example, where it can be readily accessible. The base portion 30 provides a platform upon which the device rests, and an integral information display receptacle for containing information such as the written instructions for use of the device which can be conveniently observed by a patient from the top or the bottom of the device when the device is in use. The volume chamber portion 50 provides a predetermined volume against which a patient's respiratory system is exercised for a determinable volumetric capacity to obtain the benefits of this therapy. The GRC 60 provides a readily attachable and removable display to inform a patient of the number of times a predetermined breathing exercise has been properly performed and a display to inform the patient when a predetermined breathing exercise has been properly performed. The monitoring portion 80 provides a visual display for a patient to determine the correct flow of inspiratory air to be applied by the patient's respiratory system during therapy, and in cooperation with the GRC 60 and volume chamber portion 50, permits the patient to determine the quantity of inspiratory air which has been drawn into the patient's lungs at the correct flow rate.

As best illustrated in FIGS. 1, 2, 3 and 8, the monitoring portion 80 includes an inlet port 81 formed as an opening in a front wall 83 of the monitoring portion through which a patient draws inspiratory air by means of a mouthpiece (not shown) connected to a flexible Popple tube 93. The tube 93 is sized to be securely positioned over the connecting port in which is carried a one-way valve 82 to permit a patient to draw inspiratory air through the mouthpiece 91, but which blocks the passage of expiratory air from passing back into the device. The monitoring portion 80 permits the patient to monitor the inspiratory air flow rate being applied by the patient's respiratory system during therapy, and in cooperation with the GRC 60 and volume chamber portion 50, to monitor the volume or quantity of air being inhaled.

To this end, the monitoring portion 80 includes an indicator 85 of a predetermined weight, preferably approximately 0.5 grams, which is vertically moveable between two parallel guide rails 86 (best shown in FIG. 3) which are formed between the front wall 83 and a back wall 84 of the monitoring portion 80 defining an indicator channel 75. The channel 75 in which the indicator 85 is vertically moveable, formed between the front and back walls 83, 84 and the guide rails 86, is in fluid communication with the inspiratory air inlet port 81 so that as a patient draws inspiratory air from the mouthpiece 91, the flow of air will cause the indicator 85 to rise in the channel so formed. A pair of air channels 72 and 78 are formed in the monitoring portion 80 to provide fluid communication, respectively, between the inlet port 81 and the indicator channel 75, and the inlet port 81 and the volume chamber portion 50, for a purpose to be hereinafter described in detail. A pair of indicator stops 85a are positioned to extend across the channel 75 to define the upper and lower limits of travel of the indicator 85 within the channel.

In the preferred embodiment, a window 88 or other suitable indicia such as target or demarcation lines are formed on the front wall 83 to delineate a positional range within which a patient is to keep the indicator 85 when inhaling. In this manner, a patient can monitor the proper rate of flow of the inspiratory air which is to be drawn into the respiratory system, by keeping the indicator 85 within the target area 88 of the indicator. Alternatively, when the GRC 60 is attached to the spirometer adjacent to the volume chamber portion 50, a count is maintained and an indicator lamp is illuminated for a predetermined time period when the proper rate of flow of inspiratory air is drawn into the respiratory system, and "coaches" patients to hold their breath for a particular desired period of time so that the exercise is properly performed.

On the back wall 84, a connecting oxygen inlet port 94 is formed to receive a connection from a source of oxygen. The oxygen inlet port 94 extends from the rear of the back wall 84, through the back and front walls 84 and 83 of the monitoring portion 80, and terminates at an oxygen discharge outlet 97 positioned adjacent to the inlet 81 through which a patient draws inspiratory air. The oxygen discharge outlet 97 is positioned such that the flow of oxygen is directed across an inlet 87 through which air is drawn into the device when the patient inhales through the mouthpiece 91, and not directed into the inlet 87. In this manner, the oxygen being supplied will not effect the patient created air flow applied to the device when in use. A cowling 98 partially surrounds the air inlet 87 to facilitate oxygen being drawn into the inlet 87 during use by a patient, without the flow of oxygen effecting a patient's use of the device or the monitoring of the rate of inspiratory air flow applied by a patient when using the device.

The volume chamber portion 50 includes a chamber 51 of a predetermined volume carrying a piston 53 there within. The air channel 78 forms a fluid connection between the inspiratory air inlet port 81 and the top 52 of the volume chamber 51. In this manner, when inspiratory air is drawn through the mouthpiece 91, the piston 53 will be drawn upwardly. If a patient is drawing inspiratory air at the desired target flow rate as shown by the indicator 85, the volume of air drawn into the patient's respiratory system can be determined by observing the calibrations 56 marked on the chamber 51. In one manner of operation, a slidable indicator 57 is carried on the chamber 51 and may be movably positioned by the patient to a preselected volume calibration mark 56 to facilitate convenient use of the device. Outlet ports 59 are formed in the bottom portion of the chamber 51 to facilitate the piston 53 returning to the bottom of the chamber 51 when the negative pressure from the patient's inspiration of air is terminated.

In another manner of operation, the slidable indicator 57 is moved to its lowermost position, as illustrated in the drawings, and the GRC 60 is attached to that portion of the chamber 51 upon which the indicator 57 is carried by means of a removable mounting bracket 61 which releasably connects the GRC 60 to the chamber 51. An indicator 62, formed on the mounting bracket 61, is positioned at a preselected one of the volume calibration marks 56 which corresponds to the volume of air which is desired to be drawn into the patient's lungs when using the device. A count of the number of occasions upon which a patient draws the desired volume of air into the lungs is visually displayed 63 on the GRC, and when the patient inhales a sufficient volume of air to actuate the GRC, a lamp or light emitting diode (LED) 65 is flashed for a predetermined period of time "coaching" the patient to hold the inspiration of air during the time that the LED 65 is illuminated. The manner in which the GRC 60 is actuated to record the number of occurrences in which a patient has successfully performed the desired breathing exercise, and the manner in which the LED 65 is flashed to coach the patient in the proper performance of the exercise is described in detail hereinafter with reference more particularly to FIGS. 10 and 11.

To adjust the time in which a desired quantity of inspiratory air has been inhaled by a patient at the desired rate of flow, a venturi plate 79 is positioned across the air channel 78 to provide an orifice of a predetermined size. In this manner, a standard sized air channel 78 can be utilized in manufacturing the device, with adjustments in the calibration of the flow rate required to be applied in order to attain the target rate, being determined by the size of the orifice 79*a* in the venturi plate 79, and one or more tuning openings 77 which may be formed in the front wall 83.

To use the same basic spirometer construction for both adult and child patient groupings, for example, a venturi plate 79 having a different sized air-flow-restricting orifice 79*a* can be utilized in the air channel 78 to accommodate different volumes of air being drawn at the desired flow rate, depending upon whether the spirometer is intended to be used by children or adults. For example an orifice 79*a* having an opening of approximately 0.1 by 0.05 inches has been found suitable for adults, while the same spirometer structure with a venturi plate 79 having an opening of approximately 0.1 by 0.07 inches has been found suitable for children.

As best shown in FIG. 1, the venturi plate 79 comprises two portions, one portion being attached to each of the front and back walls 83 and 84, respectively, with a part of each portion being removed to form the orifice 79*a*. For manufacturing purposes, it has been found that one of the portions forming the venturi plate 79 is best formed with the size of the part removed to form the orifice 79*a* remaining constant, while the other portion forming the venturi plate 79 may be formed with the part removed varying to change the size of the orifice 79*a* in response to the desired volume of air to be withdrawn by the user of the device. In this manner manufacturing the dimensional changes in the opening is more easily facilitated.

After the desired size of the orifice 79*a* has been determined, based upon the patients with whom the spirometer is to be used, the individual spirometers are then tested for correct calibration. The tuning openings or ports 77 are all initially open, and are selectively closed for any particular spirometer in order to more precisely control the rate of flow that must be inspired by the patient in order to attain the desired volumetric goals when in use.

Figure 3:
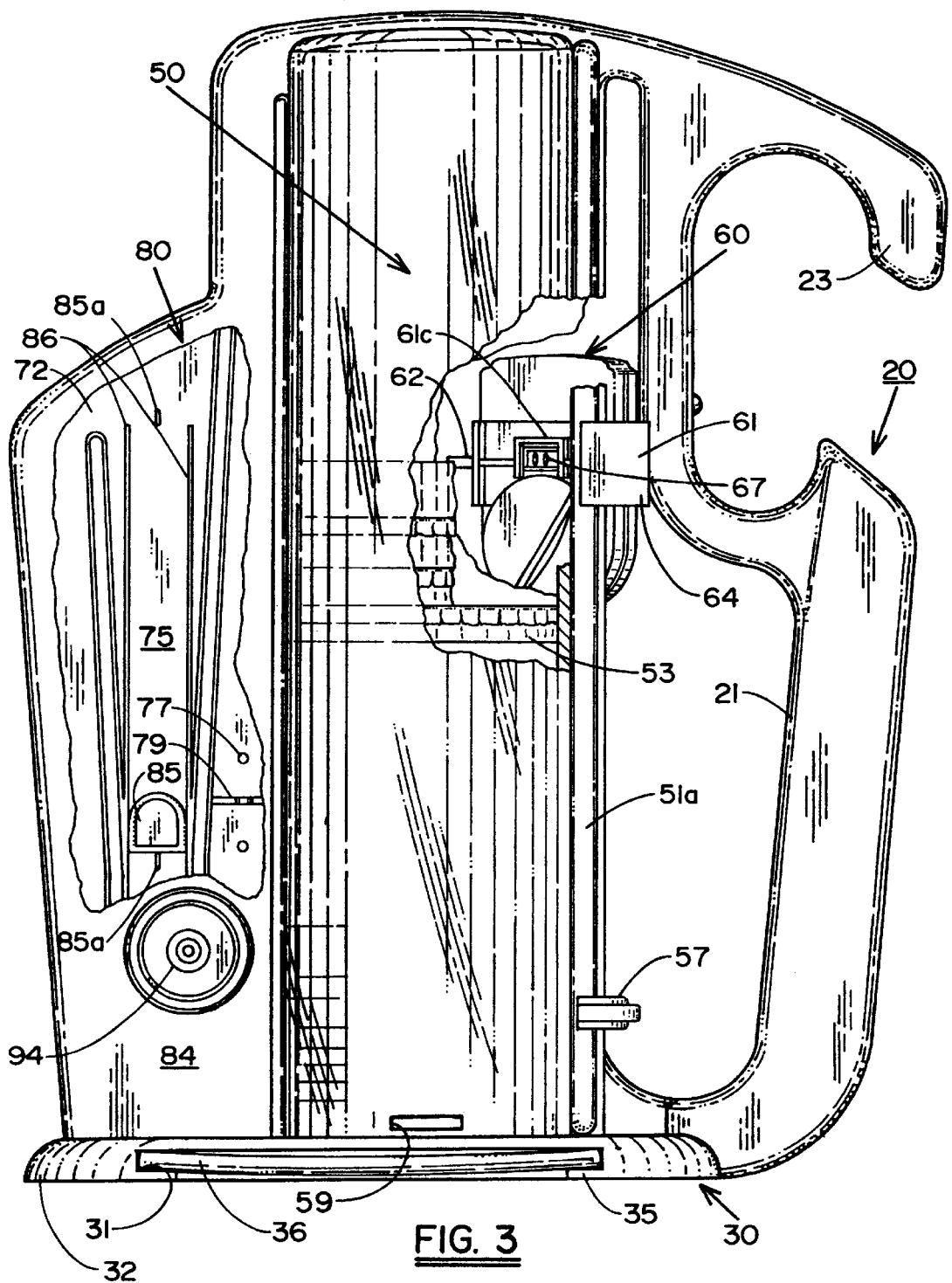
FIG. 3 is a rear elevational view of the improved incentive spirometer illustrated in FIG. 1 with portions broken away to better illustrate the internal construction thereof.
Figure 4:
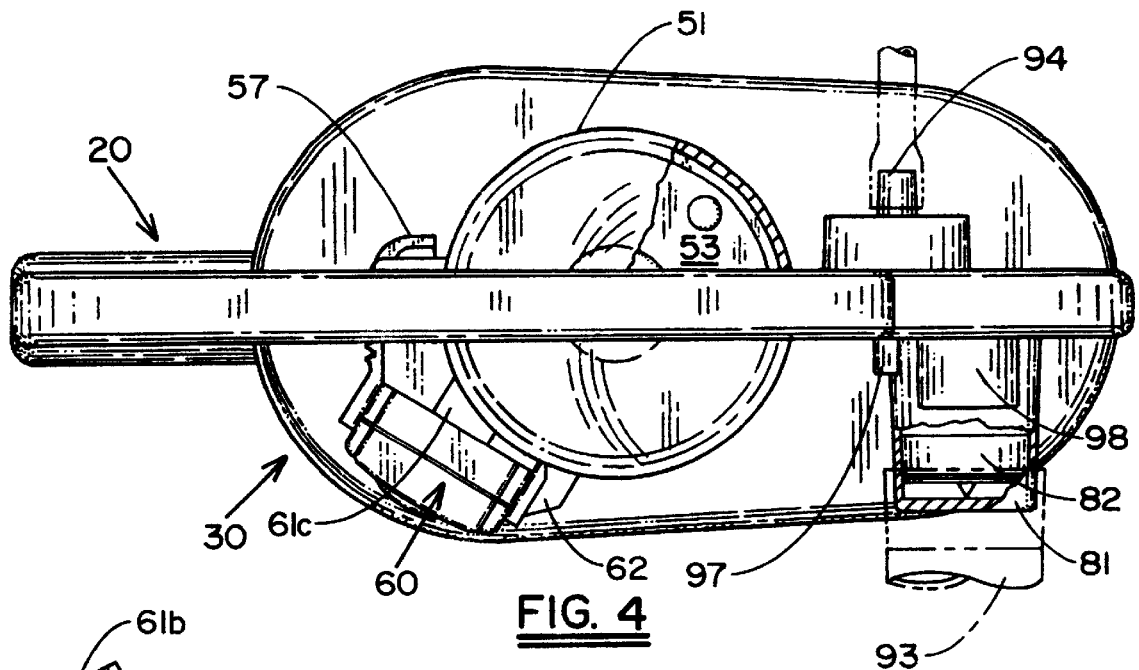
FIG. 4 is a top elevational view of the improved incentive spirometer illustrated in FIG. 1 with portions broken away to better illustrate the internal construction thereof.
Figure 8:
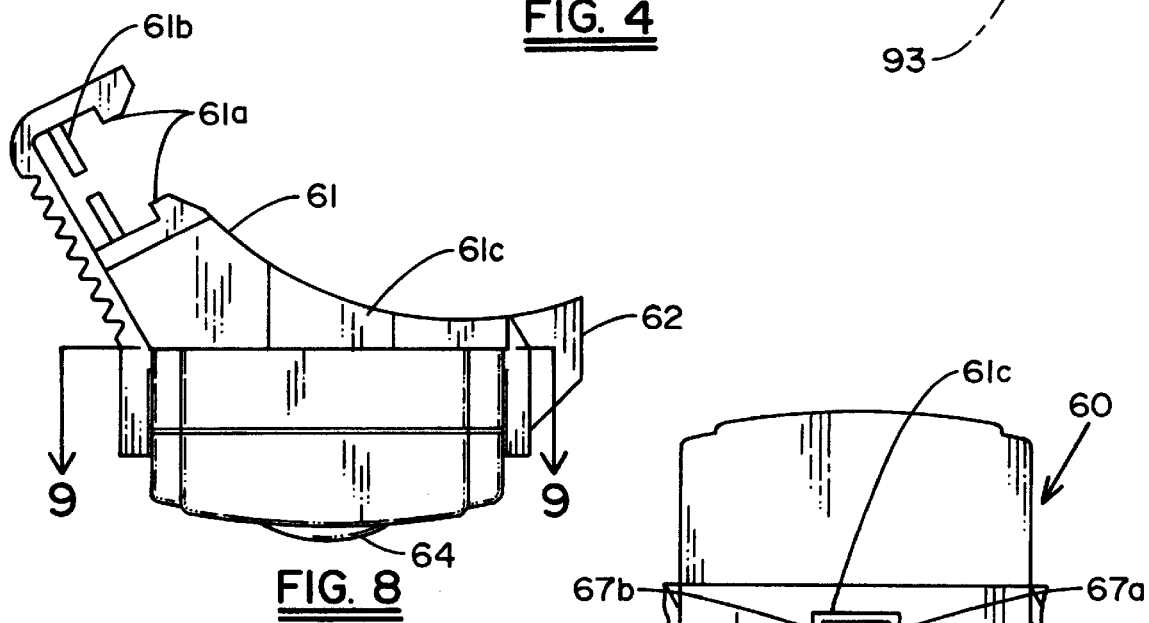
FIG. 8 is a top elevational view of the Goal Recording Counter illustrated in FIG. 5 to better illustrate the mechanism for connection to the spirometer body.
Figure 9:
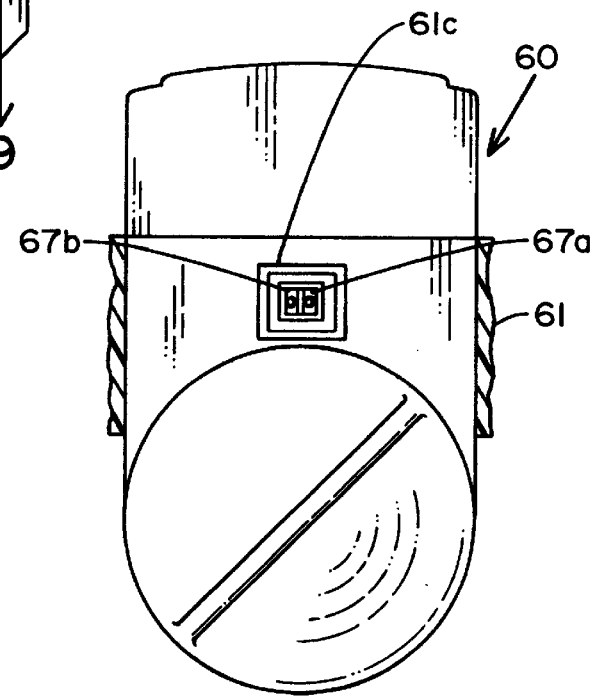
FIG. 9 is a partial rear view of the Goal Recording Counter illustrated in FIG. 5 taken along line 9—9 to better illustrate the features thereof.

In order to permit the patient to conveniently observe the instructions for use of the device, and to maintain those instructions in an accessible fashion, the base portion 30 is formed of a transparent material with an opening 31 in a skirt portion 32 of the base, best illustrated in FIG. 3. The opening 31 is formed between the top of the base and base pads 35 upon which the device stands. In this manner documentary materials, such as the instructions 36 for the use of the device, can be inserted into the base through the opening 31, and will be supported by the base pads 35 above the surface upon which the device is placed. Because the base is preferably formed of a transparent material, the instructions may be folded in a manner so that they are observable through the top and the bottom of the base to facilitate a patient's reference to them while the device is in use.

The handle portion 20 is joined at its lowermost end to the base portion 30, and at its uppermost end to the volume chamber portion 50. A closed portion is formed between a handle 21 and the chamber 51 enabling a patient to grasp and carry the device. An open hook projection 23 is formed by the uppermost part of the handle 21 enabling the device to be conveniently hung over a rail or a portion of a bed for convenient access by patients that are so confined.

Referring again to the use of the spirometer 100 with the GRC 60, as previously disclosed, the slidable indicator 57 is moved to its lowermost position and the GRC 60 is attached to the volume chamber 51 by means of the releasable bracket 61. The bracket 61, formed of a resilient plastic material, has an engaging portion 61 a which slidably engages and is secured to a vertically extending post 51 a of the volume chamber 51. The bracket 61 has an inner portion 61*b* which, along with the engaging portion 61 a, is shaped to conform to the outer cylindrical surface of the volume chamber 51 against which the back of the GRC 60 is held when the bracket 61 is attached to the chamber post 51 a. A shroud portion 6 Ic of the bracket 61 forms a 3-sided shroud about an infra-red emitter/detector 67, comprising an IR emitter 67*a* and an IR detector 67*b*, such as a Sharp Model No. GP2S40, which is carried at the back side of the GRC 60, to sense the presence of the piston 53 at the set position in the volume chamber 51. In a manner hereinafter described in detail, the infra-red emitter/detector 67 will record only the movement of piston 53 within the volume chamber 51 when the spirometer 100 is sitting on its base 30, without being falsely triggered by other occurrences.

As a patient withdraws inspiratory air from the volume chamber 51, the piston 53 carried within will rise. The GRC 60 is positioned on the chamber post 51*a* with the indicator 62 formed on the bracket 61 positioned at the desired volumetric reading 56 which it is desired that the patient obtain. When the patient has withdrawn a sufficient amount of inspiratory air to raise the piston 53 to the desired level, marked by the indicator 62, the piston 53 will reflect the infra-red signal from the emitter portion 67*a* into the detector portion 67*b* of the infra-red emitter/detector 67 whereby, upon verification of the presence of the piston 53, the electrical circuit, illustrated in FIG. 11, will cause the display 63 to be stepped incrementally to show that the desired goal has been obtained by the patient. At the same time, the coaching lamp or LED 65 will be flashed intermittently for a predetermined time period, preferably 6 seconds, to "coach" the patient to hold their breath until the light is extinguished. In this manner the patient is informed that the desired goal has been obtained and maintained for the correct period of time.

Figure 10:
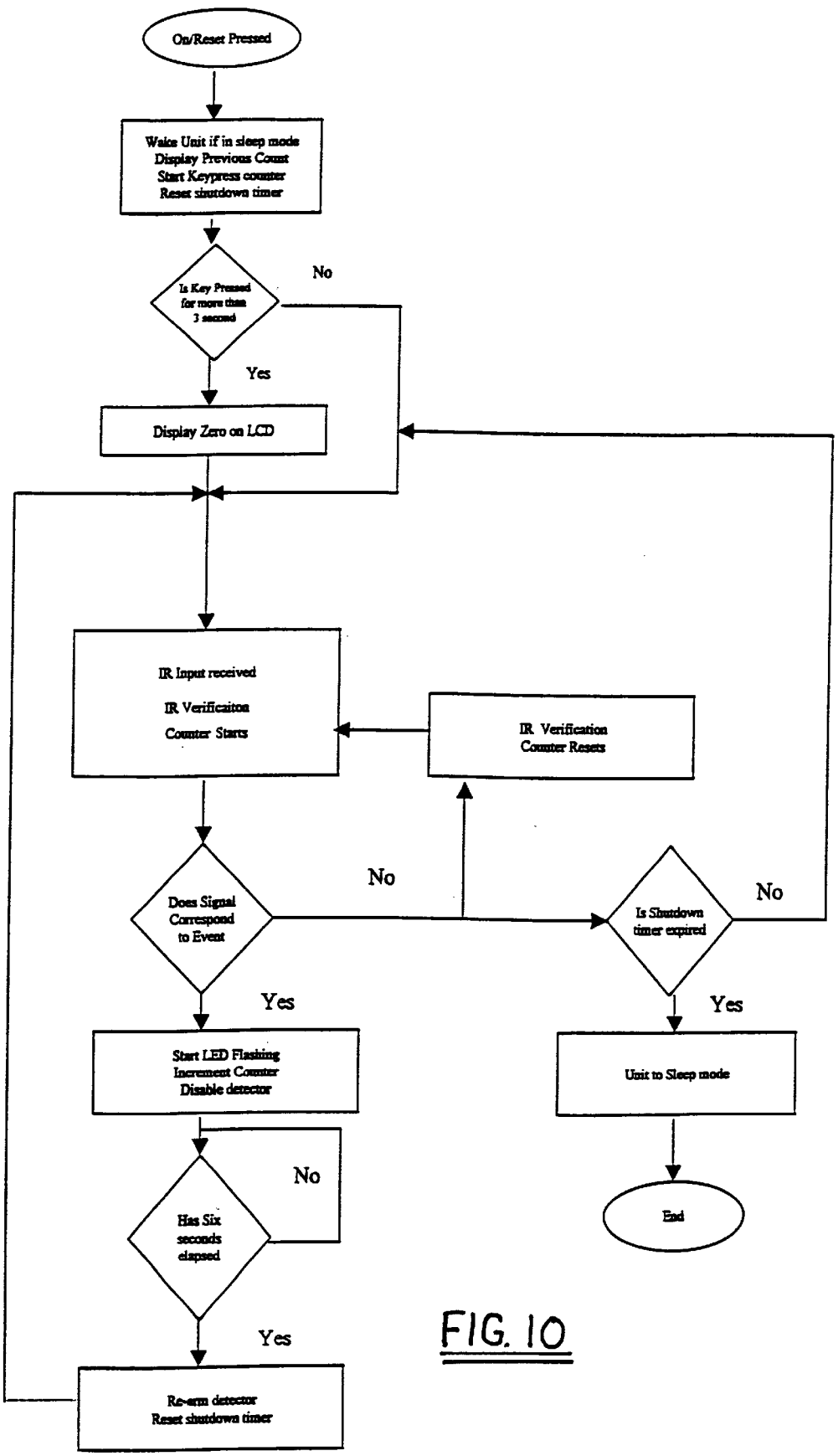
FIG. 10 is a logic block diagram or flow chart to better illustrate the manner in which the Goal Recording Counter will record the occurrence of a properly executed breathing exercise and to display to the user when the breathing exercise has been properly performed.
Figure 11:
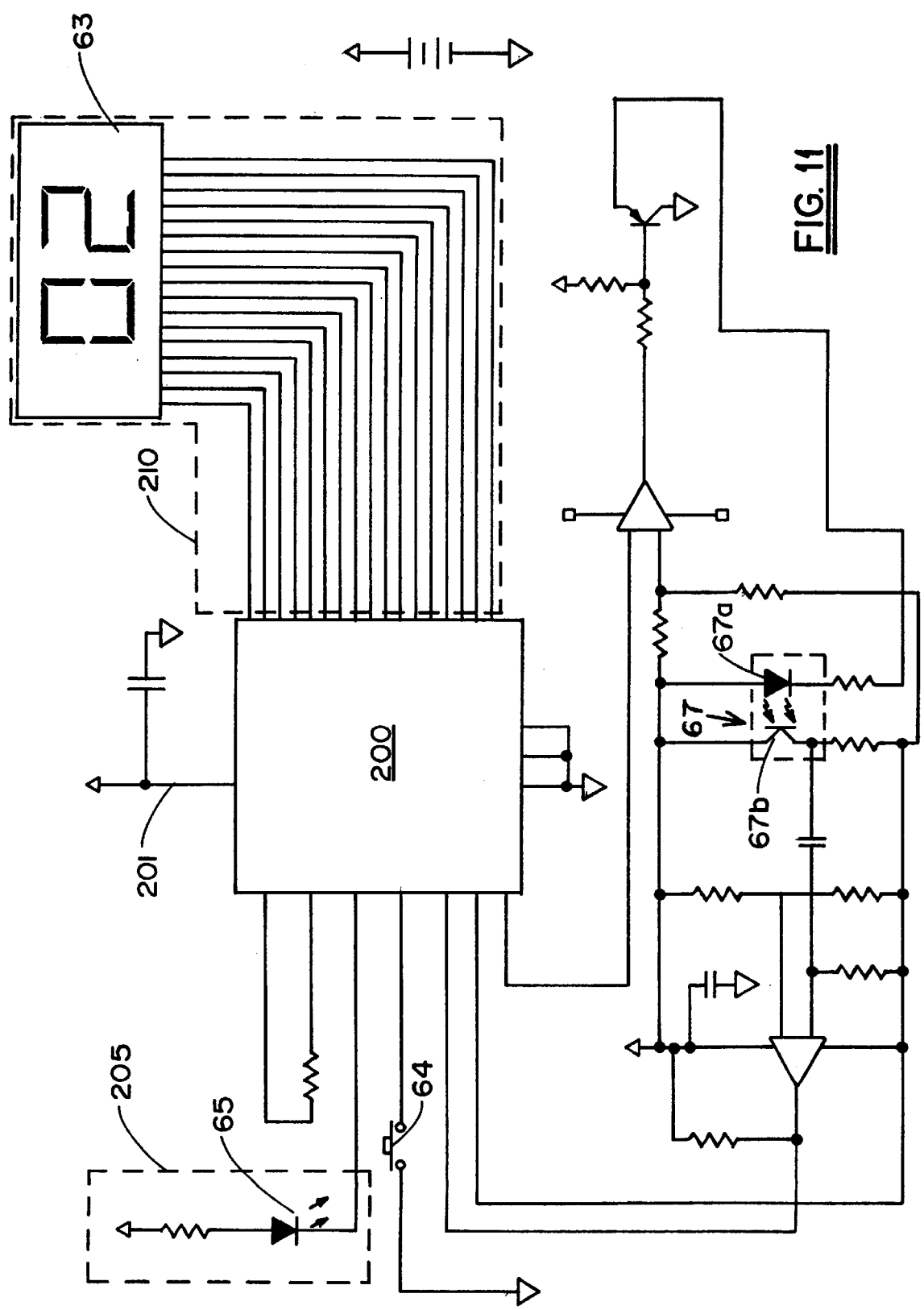
FIG. 11 is an electrical schematic of the microcontroller and circuit incorporated into the GRC for recording and displaying the occurrence of a properly executed breathing exercise and to display to the user when the breathing exercise has been properly performed.

Referring now to the logic block diagram or flow chart of FIG. 10, the operation of the GRC will be described in more detail. A preferred embodiment of an electrical circuit for effecting this operation is illustrated in FIG. 11. Initially, a power source, such as a three-volt coin type battery 201, such as a commonly available CR2032, is connected to a high-performance, four-bit microcontroller 200, such as Model W741C250, available from Winbond Electronics Corporation America, 2727 N. 1st Street, San Jose, Calif. 95134. The power supplied to the microcontroller 200 remains on at all times until the battery 201 has been exhausted and must be replaced. When an on/reset button 64 on the GRC is depressed, power is supplied to the microprocessor 200 and also the infra-red detector circuit 67, a liquid crystal display (LCD) array 210 through which a number appears on the display 63 of the GRC and to the light emitting diode (LED) indicator circuit 205 which includes the coaching LED 65 on the GRC.

When power is supplied to the GRC 60 by depressing the on/reset button 64, the GRC will have been in either a "sleep" mode, wherein the GRC has retained the count of the previously completed exercises, or in an initial state wherein the GRC will record the number of successfully completed exercises beginning from "0". Depression of the on/reset button 64 will actuate a keypress counter or reset shutdown timer circuit within the microprocessor 200 to energize a timing circuit so that after a time period the GRC will again be placed in a "sleep" mode in the event that the piston 53 is not elevated by a patient into the predetermined position within the time period set by this shutdown counter/timer.

If the on/reset button 64 is depressed for more than three seconds, the input to the LCD array 210 will display a "0" to indicate that the GRC is in condition to record a new cycle of operation beginning with the numeral "0" appearing in the window 63.

If the on/reset button 64 is depressed for less than three seconds, the LCD array is energized to display in the window 63 the retained count of how many times a patient has successfully completed an exercise since the last resetting of the GRC to "0".

Whether the GRC has been awakened from the "sleep" mode, wherein the previous count has been retained, or is placed in a mode to begin a new count from "0", the microcontroller 200 places the GRC into a condition for recording the patient's next successful completion of a breathing exercise. To this end, the emitter portion 67a of the infrared emitter/detector 67 begins emitting a modulated I-R radiation transmission to detect the presence of the piston 53, generating an event signal, if the piston is present in a manner hereinafter described in more detail, to eliminate any false triggering of the detector due to background noise or DC flooding of the emitter signal.

To prevent background noise or DC flooding from falsely triggering the infrared emitter/detector 67, the microcomputer 200 couples a clock signal of a predetermined pulse rate to the infrared emitter/detector 67, and compares the signal received by the detector 67b from the emitter 67a, with the transmitted clock signal from the microprocessor 200 to detect the occurrence of an event signal, the presence of the piston 53, to establish that the signal being received by the detector 67b is from the presence of the piston 53, rather than the occurrence of a spurious signal such as might be caused by a person passing nearby casting a shadow across the detector 67b when the GRC is in one of the operational modes to receive a signal from the emitter 67a.

In order to determine the occurrence of a proper event signal, the clock signal produced by the microprocessor 200 is coupled to the emitted 67a at a predetermined frequency, preferably 1000 Hertz. The microprocessor 200 at the same time also energizes an internal IR verification timer which is coupled to its IR detector 67b to establish a time "window", preferably 50 milliseconds, for counting the number of signal pulses, IR reflections, detected within the time period defined by the timer to verify the occurrence of an event. The microprocessor IR verification timer functions to determine if a proper number of IR signals, e.g. 20, have been received by the detector 67b within the time period or "window" established by the microprocessor 200.

If a proper event signal is received by the detector, the LED indicator circuit 205 will be energized flashing the coaching LED 65 and activating an increment counter 63 so that the patient may maintain the desired inhalation rate for a predetermined time period, preferably 6 seconds, during which the LED will remain flashing. At this time, the infrared detector 67b will be disabled. If the number of IR signals detected by detector 67b is less than its predetermined number, 20, within the time "window", no proper event has occurred and, therefore, no proper event signal is generated.

At the same time as the microprocessor emits the clock signal and the IR verification timer is energized, a shutdown timer also is energized. The shut down timer will place the GRC in the sleep mode unless a proper event signal is received to reset the shutdown or sleep timer. If the shutdown timer expires, the microprocessor 200 will shut off, and the GRC will be placed in the "sleep" mode. When a proper event signal has been received, and the LED 65 flashes for the predetermined 6 sec. time period indicative of the desired time for the patient to hold their breath, the shutdown timer will be reset. If another event signal is not received before the time set for the reset shutdown timer has expired, the microprocessor 200 will shut down, and the GRC will be placed in the "sleep" mode.

After being placed in the "sleep" mode, if the on/reset button 64 is depressed for less than 3 seconds, the GRC will "awaken" and display the retained count of the number of exercises the patient has properly performed since the last reset of the GRC to "0" to enable a patient to continue to perform and count the number of properly performed exercises. If the on/reset button 64 is depressed for 3 seconds or longer, the GRC will be reset to "0" to begin another cycle of counting properly performed exercises. When either of these events occur, the shutdown timer will be reset, and will place the GRC in the "sleep" mode if an event signal is not received by the detector from the emitter before the shutdown timer counts out. If, however, during the time period in which the reset shutdown timer is counting a patient activates the detector by inhaling at a sufficient rate to raise the piston 53 to reflect back the IR transmission from the emitter 67a, thereby generating an event signal, the process of recording a properly performed exercise begins and continues until such time as the therapy is completed and the GRC permitted to be placed in the "sleep " mode.

While this invention has been described in the specification and illustrated in the drawings with reference to preferred embodiments, the structures of which have been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

It is claimed:

1. In an incentive spirometer having a floating piston movable to a goal-responsive position in response to a patient-induced source of inspiratory air applied to a volumetric capacity indicating chamber to permit a patient to self-administer respiratory therapy by inhaling a predetermined volume of air at a desired inhalation rate, the improvement comprising:

a detachable counter adapted to be removably supported from said incentive spirometer and operable in response to a patient attaining a desired goal by inhaling a predetermined volume of air at a desired inhalation rate thereby moving said piston to a goal-responsive position in response thereto, said detachable counter including a signal emitter for emitting a signal at a predetermined rate and a signal receiver positioned to receive said signals emitted by said signal emitter in response to said piston moving to said goal-responsive position, and said detachable counter further including a controller operatively connected to said signal emitter for controlling the rate of signal emission from said signal emitter, and comparing the rate of signals received by said signal receiver to the rate of signals emitted from said signal emitter for verifying that the signals received by said signal receiver are in response to the movement of said piston into said goal-responsive position.

2. The incentive spirometer of claim 1 further including a support base having a portion thereof which is transparent, and means integral with said support base and adjacent to said transparent portion for receiving display information visually observable to a patient through said transparent portion when self-administering respiratory therapy.

3. The incentive spirometer of claim 1 further including means for applying oxygen to the source of inspiratory air inspired by a patient without effecting the inhalation rate or volumetric capacity of the patient induced source of inspiratory air as monitored or determined by the incentive spirometer.

4. The incentive spirometer of claim 3 wherein said means for applying oxygen to the source of inspiratory air inspired by a patient without effecting the inhalation rate or volumetric capacity of the patient induced source of inspiratory air as monitored or determined by the incentive spirometer comprises a source of oxygen positioned to direct a flow of oxygen adjacent to and across an inspiratory air inlet without directing the oxygen flow into the inspiratory air inlet.

5. The incentive spirometer of claim 4 wherein said means for applying oxygen to the source of inspiratory air inspired by a patient without effecting the inhalation rate or volumetric capacity of the patient induced source of inspiratory air as monitored or determined by the incentive spirometer further includes a cowling partially surrounding said inspiratory air inlet and having an opening therein facing toward said source of oxygen for receiving said oxygen therein without applying any oxygen flow from the oxygen source directly into said incentive spirometer.

6. The incentive spirometer of claim 5 further including a support base and means extending between said support base and said volumetric capacity indicating chamber forming a closed handle loop for carrying said incentive spirometer and an open hook by which said incentive spirometer may be hung.

7. The incentive spirometer of claim 1 further including means for mutually exclusively selectively controlling the patient induced inspiratory air inhalation rate applied to said volumetric capacity indicating chamber.

8. The incentive spirometer of claim 7 wherein said means for mutually exclusively selectively controlling the patient induced inspiratory air inhalation rate applied to said volumetric capacity indicating chamber and said inspiratory flow rate monitoring chamber comprises a venturi plate positioned in a path of inspiratory air flow to said volumetric capacity indicating chamber.

9. The incentive spirometer of claim 8 wherein said means for mutually exclusively selectively controlling the patient induced inspiratory air inhalation rate applied to said volumetric capacity indicating chamber and said inspiratory flow rate monitoring chamber further includes a plurality of tuning ports in said path of inspiratory air flow to said volumetric capacity indicating chamber selectively opened or closed to control the patient induced inspiratory air inhalation rate.

10. The incentive spirometer of claim 8 wherein said venturi plate is formed in two portions with a part of each portion being removed to define an orifice there through.

11. The incentive spirometer of claim 10 wherein one of said venturi plate portions has a part removed to define said orifice which is greater than the part removed from the other of said venturi plate portion.

12. The incentive spirometer of claim 1 wherein said signals emitted from said signal emitter are reflected from said piston to said signal receiver when said piston is moved to said goal-responsive position.

13. The incentive spirometer of claim 1 further including an indicia display for displaying the number of times a patient has moved said piston to said goal-responsive position.

14. The incentive spirometer of claim 13 wherein said indicia display is operatively connected to said controller for sequential advancement of said indicia display in response to the movement of said piston to said goal-responsive position.

15. The incentive spirometer of claim 1 further including reset means operable in a first sequence to energize said controller and operable in a second sequence for resetting said detachable counter to "0" for beginning a new cycle of operation.

16. The incentive spirometer of claim 1 wherein said controller further includes a timer for shutting down said controller in the event no signals are received by said signal receiver within a set period of time.

17. The incentive spirometer of claim 16 wherein upon shut down said controller retains the count of the number of times said piston has been moved into said goal-responsive position.

18. The incentive spirometer of claim 15 wherein operation of said reset means in said first sequence energizes said controller and retains the count of the number of times said piston has been moved into said goal-responsive position.

19. The incentive spirometer of claim 1 further including means operatively coupled to said controller for producing a timed display signal in response to said piston moving to said goal-responsive position.

20. An event detecting and recording system comprising:

a controller including a resettable counter operable in a first timed sequence to display an accumulated count of goal-responsive events and operable in a second timed sequence to reset an accumulated count of goal-responsive events to "0";

an indicia display operatively connected to said resettable counter for displaying the occurrence of goal-responsive events;

a signal emitter operatively connected to said controller for emitting a signal at a predetermined rate to signal the occurrence of a goal-responsive event;

a signal receiver operatively connected to said controller for receiving said signal from said signal emitter to determine the occurrence of a goal-responsive event; and said controller further including means for comparing a signal received by said signal receiver with said signal emitted from said signal emitter to verify the occurrence of a goal-responsive event.

21. The event detecting and recording system of claim 20 wherein said signal emitted by said signal emitter is coupled to said signal receiver only upon the occurrence of a goal-responsive event.

22. The event detecting and recording system of claim 20 wherein said resettable counter is sequentially advanced upon the occurrence of a goal-responsive event to display an accumulated count of said goal-responsive events.

23. The event detecting and recording system of claim 20 further including a timer for terminating the operation of said controller in the event a goal-responsive event is not verified by said controller within a period of time determined by said timer.

24. The event detecting and recording system of claim 23 wherein upon termination of the operation of said controller, the count of said goal-responsive events is retained until said resettable counter is reset by being operated in said second time sequence.

25. The event detecting and recording system of claim 20 wherein said controller produces a timed display signal upon the verification of the occurrence of a goal-responsive event.

* * * * *